United States Patent [19]

Beachey

[11] 4,454,121

[45] Jun. 12, 1984

[54] SYNTHETIC PEPTIDES CORRESPONDING TO ANTIGENIC DETERMINANTS OF THE M PROTEIN OF *STREPTOCOCCUS PYOGENES*

[75] Inventor: Edwin H. Beachey, Memphis, Tenn.

[73] Assignee: The University of Tennessee Research Corporation, Knoxville, Tenn.

[21] Appl. No.: 402,355

[22] Filed: Jul. 27, 1982

[51] Int. Cl.³ .................... A61K 37/00; C07C 103/52
[52] U.S. Cl. .............................. 424/177; 260/112.5 R
[58] Field of Search .................. 260/112.5 R; 424/177

[56]  References Cited

PUBLICATIONS

E. H. Beachey et al., The Journal of Experimental Medicine 150, (1979), pp. 862-877.

*Primary Examiner*—Delbert R. Phillips
*Attorney, Agent, or Firm*—Weiser & Stapler

[57]  ABSTRACT

Synthetic peptides corresponding to antigenic determinants of the M protein of *streptococcus pyogenes* are disclosed. These peptides are useful for vaccination against *streptococcus pyogenes* bacteria.

12 Claims, No Drawings

SYNTHETIC PEPTIDES CORRESPONDING TO ANTIGENIC DETERMINANTS OF THE M PROTEIN OF STREPTOCOCCUS PYOGENES

This invention relates to synthetic peptides which correspond to antigenic determinants of the M protein of *S. pyogenes*. More particularly, the invention relates to small synthetic immunogenic peptides which are able to elict opsonic antibodies which are type-specific for type 24 streptococci and which are not serologically cross-reactive with tissue antigens of the human or of the host heart.

Recently Audibert et al. actively immunized laboratory animals against diptheria toxin using a chemically synthesized oligopeptide. Audibert, F. et al. Nature 289, 593–594 (1981). This work does not show however, that a synthetic peptide antigen can raise antibodies which promote phagocytosis and killing of a bacterial pathogen.

U.S. Pat. No. 4,284,537, issued Aug. 18, 1981, disclosed the amino acid sequence of two peptide fragments derived from M protein. It also disclosed that each of these natural fragments, when covalently linked to a carrier such as polylysine, was able to elict type-specific opsonic antibodies effective against *Streptoccocus pyogenes*. Each of these fragments was a natural extract, and each contained 35 amino acids.

The mechanism whereby streptococcal infections give rise to complications such as rheumatic fever have remained to a large extent unexplained to date. Because the sera of some patients with rheumatic fever show serological cross-reactivity between heart tissue antigens and certain streptococcal antigens, it has been feared that immunization with intact M-protein vaccines may lead to rheumatic heart disease. See, for instance, Stollerman, *Rheumatic Fever and Streptococcal Infection* (Greene and Stratton, New York, 1975). It has been observed that rabbits and mice immunized with cyanogen bromide fragments (CB6 or CB7) of type 24 M protein containing only 35 amino acid residues each developed opsonic and protective antibodies against type 24 streptocci.

In accordance with the invention, one of these peptides (CB7), has now been chemically synthesized (S-CB7), and it was discovered that protective immunity in laboratory animals is induced by S-CB7 covalently linked to polylysine. In addition, it was found that one of the protective determinants resides in a peptide fragment of S-CB7 containing only 12 amino acid residues. See also Beachey, et al, Nature, 292, 457–459 (1981), published July 30, 1981. Other novel aspects of the invention are disclosed further herein.

The immunogenicity of small peptide fragments is encouraging for the development of safe and effective vaccines against those streptococcal infections that initiate rheumatic fever and rheumatic heart disease. The efficacy of very small peptides would permit disposal of a large portion of the M protein molecule and, therefore, should reduce the chances of eliciting immunological cross-reactions against host tissues. Thus, the continued identification of peptide structures responsible for protective immunity should yield a pool of small peptides that may eventually be synthesized and administered safely to humans as vaccine broadly protective against many serotypes of streptococci, particularly against those strains that trigger post-streptococcal sequelae.

It is, therefore, an object of the present invention to provide a small, synthetic peptide which is effective in eliciting opsonic antibodies which are type-specific for *Streptococcus pyogenes* and which do not show serological cross-reactivity with tissue antigens of the human heart.

It is also an object of the present invention to provide a small, synthetic peptide which is effective to elicit cellular immunity to *Streptococcus pyogenes* without providing effective humoral immunity.

In accordance with the invention, the carriers which are used to make the conjugate with the peptide sequences of the invention are any "natural" or synthetic carrier. The term carrier is a recognized term in the art and literature and sometimes is referred to as "coupler" or as "protein carrier".

Natural carriers used in accordance with the invention are known and are typically, BSA or OVA. Synthetic carriers are, typically, polylysine. Hapten carriers are well known in the literature and need not be further described here to one skilled in the art. Generally, these carriers are covalently linked to the protein sequence.

The S-CB7 polypeptide fragment of type 24 M protein and a dodecapeptide starting at residue 18 and ending at residue 29 (S18-29CB7) were synthesized according to the method of R. B. Merrifield described in J. Am. chem. Soc. 85, 2149–2155 (1963), and purified by reverse-phase HPLC on Ultrasphere ODS2 (Whatman) columns (Penninsula laboratories). The S18-29CB7) peptide overlaps two subpeptides derived from trypsin digestion of lysyl-blocked CB7 (see below). Amino acid analyses confirmed the identity of the synthetic peptides. Automated Edman degradation to the penultimate residue gave the amino acid sequence of S-CB7 as Asn-Phe-Ser-Thr-Ala-Asp-Ser-Ala-Lys-Ile-Lys-Thr-Leu-Glu-Ala-Glu-Lys-Ala-Ala-Leu-Ala-Ala-Arg-Lys-Ala-Asp-Leu-Glu-Lys-Ala-Leu-Glu-Gly-Ala-Met.

This sequence differs from that of native CB7 fragment in that the COOH-terminal residue of S-CB7 is methionine, not homoserine.

The amino acid sequence of the S18-29CB7 peptide differed from the corresponding segment of CB7 by the addition of a glycine tripeptide at the COOH terminal, which is used as a leash in the synthesis of the peptide.

The properties of the peptides of the invention are shown below.

Three rabbits immunized with 25 nmol of S-CB7 emulsified in complete Freund's adjuvant (CFA) according to the method described in Beachey, E. H. et al. J. biol Chem. 255, 6284–6289 (1980), developed antibody titers at 6 weeks of 1:400, 1:1,280 and 1:25,600, respectively, as determined by enzyme-linked immunosorbent assays (ELISAs). However, only the serum showing the highest ELISA titer was capable of opsonizing type 24 streptococci. The native CB7 is not immunogenic alone so this activity of synthetic S-CB7 was noted with interest.

Three additional rabbits were immunized with 25 nmol of S-CB7 covalently conjugated to polylysine (molecular weight (MW) 35,000) and emulsified in CFA. The sera of all three rabbits showed good antibody responses as measured by ELISAs or opsonic antibody assays (FIG. 1). In bactericidal assays using types 5, 6 and 24 streptococci, the immune sera were able to promote phagocytosis and killing of only the homologous type 24 streptococci, indicating that the humoral responses to the synthetic peptide fragment are type-specific.

Sera collected at 2-week intervals were assayed for antibodies to type 24 M protein absorbed to the walls of plastic cuvettes by the ELISA method. ELISA titers are expressed as the reciprocal of the highest dilution of serum giving an absorption >0.1 at 405 nm. Opsonic antibodies were assayed as described in Beachey, E. H. et al. in P.N.A.S. (U.S.A.) 75, 3163–3167 (1978). Briefly, the test mixture consisted of 0.4 ml of fresh heparinized (10 U ml$^{-1}$) human blood, 0.05 ml of a standard suspension of streptococci and 0.05 ml of various dilutions of test serum. The number of streptococcal units per leukocyte was ~10. The percentage of neutrophilic leukocytes counted that ingested one or more bacteria was estimated by microscopic examination of stained smears prepared from a drop of test mixture after incubation for 30 min. The opsonic antibody titers are expressed as the reciprocal of the highest twofold dilution of test serum in three separate tests that promoted phagocytosis of streptococci in $\geq$10% of the neutrophils counted after incubation at 37° C. for 30 min; the same organisms in the presence of preimmune rabbit serum were phagocytosed by $\leq$2% of neutrophils in each test. Antisera giving titers >1:4 all produced phagocytosis in the range 40–70% when undiluted. The results of these phagocytosis tests were confirmed by indirect bactericidal tests performed as described in Beachey, E. H. & Stollerman, G. H., J. exp. Med. 134, 351–365 (1971). Type specificity of the sera was confirmed by the failure of the S-CB7 immune sera to promote phagocytosis and killing of heterologous type 5 and type 6 streptococci. The immune response to synthetic S-CB7 was greater and appeared sooner than the response to native CB7.

Agar gel diffusion tests using the immune rabbit sera gave precipitin arcs between the polylysine conjugates of the synthetic and the native CB7, as well as with the intact pepsin-extracted type 24 M protein (pep M24) molecule, which further confirms that the synthetic and native CB7 peptide fragments are immunochemically identical. Neither type 5 nor type 6 M protein was immunoreactive with anti-CB7 antiserum. None of the S-CB7 immune sera tested was reactive with frozen sections of human heart tissue assayed by immunofluorescene as described in Beachey, E. H. et al., J. exp. Med. 150, 862–877 (1979).

To demonstrate the protective capacity of the antisera against S-CB7, mice were passively immunized with a pool of the immune rabbit sera and challenged after 24 h with the live type 24 or type 6 streptococci. The results (See Table 1) clearly show the type-specific protective capacity of the immune sera and indicate that the S-CB7 peptide contains at least one protective antigenic determinant of type 24 streptococci.

TABLE 1

Protection of Mice Against Challenge Infections with Type 24 Streptococci by Sera of Rabbits Immunized with S-CB7

| Serum used to immunize mice passively | LD$_{50}$ in mice challenged with: | |
|---|---|---|
| | Type 6 streptococci | Type 24 streptococci |
| Preimmune serum | <500 (2/15) | <500 (3/15) |
| Pooled (three rabbits) immune anti-S-CB7 serum | <500 (2/15) | 3,500,000 (14/15) |

Three rabbits were immunized intracutaneously with 25 nmol of S-CB7 conjugated to polylysine (MW≃35,00) and emulsified in CFA. The initial immunizing dose was followed 1 week later by the same dose emulsified in incomplete Freund's adjuvant and injected subcutaneously. Preimmune and immune sera, obtained before immunization and 6 weeks after the initial immunizing dose, respectively, were pooled and white Swiss mice injected intraperitoneally with 0.2 ml of either serum. The mice were challenged 24 hours later by the same route with various does 500-4$\times$10$^6$ colony-forming units of type 6 or type 24 streptococci. The survivals were recorded over a 7-day period and are shown in parentheses in Table 1 as the number of survivors per number of challenged mice.

To determine whether protective antigenic determinants resided in yet smaller peptide fragments, the CB7 peptide was cleaved at its arginine residue by trypsin, after blocking lysyl residues with recrystallised maleic anhydride (to a molar excess of 20 over the total number of lysyl residues) according to the methods described in Beachey et al. PNAS (USA) 75, 3163–3167 (1978) and Butler et al, Biochem. J. 112, 679–689 (1969). After digestion with trypsin (TPCK (tosyl-phenylethyl-chloromethyl-ketone)-treated, Worthington) at an enzyme/substrate ratio of 1:50 (w/w) in 0.05 M NH$_4$HCO$_3$, pH 8.3, the lysyl residues were demaleyated using pyridine/acetate (1:10), pH 3.0 at 60° C. for 6 hours. The demaleyated peptides were then HPLC-separated on a column of Ultrasphere ODS2 equilibrated with 0.01 M phosphate buffer, pH 7.2, and eluted on a gradient of 0–40% acetonitrile according to the method described in River, J. E., J. Liq. Chromatogr., 343–353 (1978). In this way, a 12-residue COOH-terminal and a 23-residue NH$_2$-terminal peptide were purified and then tested for their ability to inhibit opsonic antibodies according to the method described in Beachey et al., J. biol. Chem. 255, 6284–6289 (1980). For 50% inhibition of opsonization of type 24 streptococci, 9 nmol of the 23-residue, NH$_2$-terminal peptide and 20 nmol of the 12-reside, COOH-terminal peptide of CB7 were needed, compared with only 1.6 nmol of a mixture of the two peptides and 0.8 nmol of the uncleaved CB7 peptide. The greater activity of the mixture of the two peptide fragments of CB7 indicates that CB7 contains at least two distinct type-specific protective determinants, and that one of these resides in a peptide containing only 12 amino acid residues. The synthetic dodecapeptide overlapping these two peptides (residues 18–29) had no opsonic inhibitory effect in doses as high as 100 nmol, suggesting that neither immunodeterminant is included in this dodecapeptide. However, the possibility that the COOH-terminal triglycine residues may interfere with antibody binding at that end of the dodecapeptide has not been excluded.

In contrast to the type specificity of the humoral immune responses to S-CB7, the cellular immune responses were highly cross-reactive. The lymphocytes of S-CB7-immunized rabbits were equally responsive to a heterologous type 5 M protein and an homologous type 24 M protein (Table 2). Moreover, immunization of rabbits with the synthetic dodecapeptide (S18-29CB7), although not providing effective humoral immunity, induced cellular immunity to both serotypes of M protein similar to that seen after immunization with S-CB7 (Table 2). The lymphocytes from none of the animals responded to S-CB7 or S18-29CB7, indicating that these peptides were of insufficient molecular size to elicit the in vitro blastogenic response of sensitized lymphocytes.

Heparinized (100 U ml$^{-1}$) peripheral blood was obtained from rabbits 2–6 weeks after immunization (see Table 1 legend) by cardiac puncture. Mononuclear cells were isolated by Ficoll-Hypaque gradient centrifugation. Lymphocytes were washed three times and resuspended in RPMI 1640 (Gibco) supplemented with penicillin (100 U ml$^{-1}$), streptomycin (100 ug ml$^{-1}$), L-glutamine (2 mM) and HEPES buffer (25 mM). Lymphocytes ($2 \times 10^5$) were incubated at 37° C. with 50 ug per culture of each antigen tested in 96-well microculture plates (Falcon Plastics) in a total volume of 200 ul supplemented with 5% heat-inactivated fetal calf serum. Control cultures were incubated in the same volume of medium without antigen. Eighteen hours before collecting, 1 uCi of $^3$H-thymidine (specific activity 2 Ci mmol$^{-1}$, Research Products International) in 25 ul culture medium was added to each well. All cultures were collected after 5 days using multiple automated sample harvester and the cells assayed for radioactivity in a liquid scintillation counter. Control animals were injected with the same volume of CFA emulsified in 0.15 M NaCl without antigen.

TABLE 2

Blastogenic responses of lymphocytes from rabbits immunized with S-CB7 or S18-29CB7 fragments of type 24 M protein

| Rabbit | Immunizing antigen | Mean c.p.m. (±s.e.m.) of lymphocytes cultured with: | | |
|---|---|---|---|---|
| | | Control | M5 | M24 |
| 8026 | S-CB7 | 98 ± 23 | 3,743 ± 411 | 4,721 ± 479 |
| 8027 | S-CB7 | 181 ± 28 | 12,684 ± 1,454 | 829 ± 124 |
| 8028 | S-CB7 | 156 ± 31 | 43,391 ± 3,094 | 36,449 ± 5,416 |
| 7919 | S18-29CB7 | 415 ± 27 | 11,521 ± 3,081 | 12,038 ± 243 |
| 7921 | S18-29CB7 | 135 ± 31 | 17,056 ± 3,081 | 3,575 ± 1,265 |
| 8020 | S18-29CB7 | 705 ± 59 | 12,487 ± 918 | 4,916 ± 362 |
| 8007 | CFA (control) | 76 ± 102 | 64 ± 12 | 40 ± 2 |
| 8008 | CFA (control) | 31 ± 11 | 153 ± 25 | 83 ± 25 |

The significance of the cell-mediated cross-reactions between synthetic peptide fragments and heterologous M proteins is unclear; structural similarities between the M proteins may account for these cross-reactions as well as for the high degree of cellular immunity to various M proteins recently observed in lymphocytes from human adults as well as cord blood of newborn infants.

The synthetic S-CB7 of type 24 streptococcal M protein represents a 35-amino acid fragment of the parent molecule, which consists of 376 amino acid residues. The molecule has previously been shown to consist of repeating covalent structures, the first 20 residues of CB7 being identical to the corresponding regions of four other peptide fragments (CB3, CB4, CB5 and CB6). Two additional fragments (CB1 and CB2), each with a MW of 10,000, have NH$_2$-terminal amino acid sequences which are different from the smaller peptide fragments but are identical to each other and to the intact pepsin-extracted M protein (pep M 24) molecule for at least the first 27 residues.

In addition, the 12 COOH-terminal residues of CB1 and CB2 were found to be identical to those of each of the smaller peptides. It was particularly intriguing that one of the protective determinants was shown to reside in this 12-residue peptide, which is repeated seven times in the pep M24 molecule. Because of the repetitive nature of the primary structure of the M protein molecule it is not surprising retrospectively that antibody directed against such a small segment of the molecule proved to be opsonic and presumably protective. The repetition of the determinant would provide multiple sites of interaction with the immunoglobulin molecules. Such interaction at multiple sites seems to be necessary for optimal opsonization of M protein-containing streptococcal cells.

The invention also encompasses biologically active compositions comprising the antigen and an immunostimulant and wherein the antigen is administered with the immunostimulant. CFA is one such immunostimulant. Other natural and synthetic immunostimulants are well known in the art. The administration need not be concurrent; one may preceed the other, in part or all of it. What is important is that the two components are present in the system of the mammal concurrently.

The biological compositions of the invention can be in any suitable form for administration to the mammal, whether a human or animal. Such are known in the art.

Solid compositions for oral administration include compressed tablets, pill, powders and granules. In such solid compositions, at least one of the active ingredients is admixed with at least one inert diluent such as starch, calcium carbonate, sucrose or lactose. These compositions may also contain additional substances other than inert diluents, e.g. lubricating agents, such as magnesium stearate, talc and the like.

Liquid compositions for oral administration include pharmaceutically-acceptable emulsions, solutions, suspensions, syrups and elixirs containing inert diluents commonly used in the art, such as water. According to the invention, the compounds for oral administration also include capsules of absorbable material, such as gelatin, containing said active component with or without the addition of diluents or excipients.

Preparations according to the invention for parenteral administration include sterile aqueous-organic, and organic solutions, suspensions and emulsions. Examples of organic solvents or suspending media are propylene glycol, polyethylene glycol, vegetable oils, such as olive oil, and injectable organic esters, such as ethyl oleate. These compositions can also contain adjuvants such as stabilising, preserving, wetting, emulsifying and dispersing agents. Aqueous compositions are by far preferred.

The percentages of active component in the said composition and method for causing the desired biological effect, (e.g. immunological or hormonal) inhibitory can be varied so that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus be determined best by the clinician considering all criteria and utilizing the best judgment on the patient's behalf. For practical considerations, the proportion may vary for about 0.01 to 20%, or higher, of active ingredient per composition. What is needed is that at least the minimum effective amount to give the desired effect be present.

Other aspects of the invention will readily become apparent to one skilled in the art.

I claim:

1. A synthetic polypeptide having the following amino acid sequence:

Asn-Phe-Ser-Thr-Ala-Asp-Ser-Ala-Lys-Ile-Lys-Thr-Leu-Glu-Ala-Glu-Lys-Ala-Ala-Leu-Ala-Ala-Arg-Lys-Ala-Asp-Leu-Glu-Lys-Ala-Leu-Glu-Gly-Ala-Met.

2. A synthetic polypeptide, having the following amino acid sequence:

Ala-Ala-Leu-Ala-Ala-Agr-Lys-Ala-Asp-Leu-Glu-Lys-Gly-Gly-Gly.

3. A peptide fragment having the following amino acid sequence:

Lys-Ala-Asp-Leu-Glu-Lys-Ala-Leu-Glu-Gly-Ala-Met.

4. A peptide fragment having the following amino acid sequence:

Asn-Phe-Ser-Thr-Ala-Asp-Ser-Ala-Lys-Ile-Lys-Thr-Leu-Glu-Ala-Glu-Lys-Ala-Ala-Leu-Ala-Ala-Arg.

5. A synthetic antigen for eliciting type-specific opsonic antibodies to *Streptococcus pyogenes*, said antigen comprising a polyvalent linkable carrier covalently linked to the polypeptide of claim 1.

6. A synthetic antigen for eliciting cellular immunity to *Streptococcus pyogenes*, said antigen comprising a polyvalent linkable carrier covalently linked to the polypeptide of claim 2.

7. The synthetic antigen of claim 5 or 6 wherein the polyvalent linkable carrier is a natural protein carrier.

8. The synthetic antigen of claim 5 or 6 wherein the carrier is a synthetic polymer.

9. The synthetic antigen of claim 12 wherein the carrier is polylysine.

10. A biologically active composition which comprises a biologically acceptable diluent, and immunostimulant and in an amount sufficient to cause a biologically positive response the antigen of claims, 1, 2, 3, 4, 5 or 6, which composition is immunogenic with respect to *Streptococcus pyogenes*.

11. The biologically active composition of claim 10 wherein the immunostimulant is CFA or a synthetic immunostimulant.

12. A method for controlling streptococcal infections in a mammal which comprises administering to a mammal in a dose sufficient to control *Streptococcus pyogenes*, the composition of claim 10, and controlling *Streptococcus pyogenes* in said mammal.

* * * * *